United States Patent [19]
Grendahl

[11] Patent Number: 4,624,669
[45] Date of Patent: Nov. 25, 1986

[54] CORNEAL INLAY WITH HOLES
[75] Inventor: Dennis T. Grendahl, Orono, Minn.
[73] Assignee: Surgidev Corporation, Santa Barbara, Calif.
[21] Appl. No.: 654,962
[22] Filed: Sep. 26, 1984
[51] Int. Cl.⁴ .................................................. A61F 2/14
[52] U.S. Cl. ........................................ 623/5; 128/1 R; 623/11
[58] Field of Search ............................ 3/13, 1; 128/1 R; 623/4, 5, 6, 11

[56] References Cited
U.S. PATENT DOCUMENTS
2,714,721  8/1955  Stone .................................... 3/13 X
3,699,956 10/1972  Kitrilakis et al. ....................... 3/1 X FOREIGN PATENT DOCUMENTS
3208729  9/1983  Fed. Rep. of Germany ............ 3/13
2081469  2/1982  United Kingdom ..................... 3/13

OTHER PUBLICATIONS
Corneal Surgery (book) by Louis J. Girard, Advanced Techniques in Ophthalmic Microsurgery, Vol. Two, 1981, pp. 143-149, FIG. 6-2 on pp. 146-147.

Primary Examiner—Ronald L. Frinks
Attorney, Agent, or Firm—Hugh D. Jaeger

[57] ABSTRACT

A corneal inlay for implant within the cornea and of a material such as polysulfone or PMMA, including a plurality of small holes or pores to pass nutrients and fluids from the bottom surface layer of the cornea to the top surface layer of the cornea. The holes can be round, the holes can be rectangular in configuration, or the holes can be slits in configuration, preferably small enough so that the holes are not visible to the naked eye. The holes can be particularly slots of a finite width and length, either adjacent to the edges of the inlay or across the surface of the inlay. The holes also provide for breathing and passage of nutrients and fluids, as well as oxygen transmission, between the upper and lower surfaces of the cornea in which the inlay has been implanted.

6 Claims, 5 Drawing Figures

CORNEAL INLAY WITH HOLES

BACKGROUND OF THE INVENTION

1. Field of the Invention

The present invention relates to a surgically implanted lens, and more particularly, pertains to a corneal inlay with holes which is implanted in the cornea.

2. Description of the Prior Art

The prior art corneal inlays implanted into the cornea, may exhibit certain tendencies which do not provide for the passage of nutrients from the bottom layer to the top layer of the cornea; that is, from the underside to the top side of corneal tissue with the corneal inlay implanted therebetween. While corneal transplants are a relatively new procedure in the ophthalmology field, there is concern among the medical community that nutrients may not be able to pass to the upper layer of the cornea from the bottom layer through the corneal inlay.

The present invention overcomes the disadvantages of the prior art, by providing a corneal inlay with holes for passage of nutrients or fluids, etc.

SUMMARY OF THE INVENTION

The general purpose of the present invention is to provide a corneal inlay with holes to provide for passing of nutrients and fluids from the lower layer of the cornea to the upper layer of the cornea through the corneal inlay.

According to one embodiment of the present invention, there is provided a corneal inlay of a material, such as polysulfone or PMMA or the like, etc., and a plurality of holes or pores of a predetermined geometrical shape positioned through the thickness of the corneal inlay. The holes can either be dispersed about the adjacent edge of the corneal inlay, or can be dispersed randomly throughout the surface area of the corneal inlay. The holes are of such a diameter so as not to be visible by the eye and allow for nutrients to pass from the bottom layer to the top layer of the corneal inlay. The holes can also be clustered together in groups, or equally spaced.

One significant aspect and feature of the present invention is a corneal inlay which is provided with at least one hole or more, preferably a plurality of holes, which provides for passage of nutrients and fluids which are so ever important in maintaining the tissue and endothelial cells of the cornea.

Another significant aspect and feature of the present invention are holes in a corneal inlay which are so small so that the holes cannot be observed by the patient when the corneal inlay is implanted into the cornea of the eye so as not to interfer with the patients's vision.

Having thus described embodiments of the present invention, it is the principal object hereof to provide a corneal inlay with holes.

One object of the present invention is a corneal inlay with at least one hole, preferably a plurality of holes derived for passing of nutrients from the bottom surface of the cornea to the top surface of the cornea; that is, between the opposite sides of the cornea with respect to the corneal inlay transplant.

DESCRIPTION OF THE PREFERRED EMBODIMENTS

Figure 1:
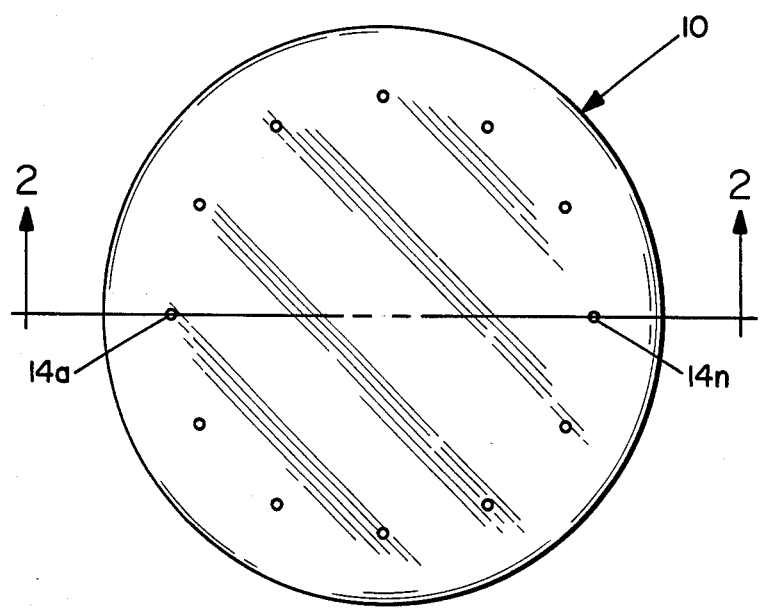
FIG. 1 illustrates a top view of a corneal inlay with a plurality of holes about an outer edge.
Figure 2:
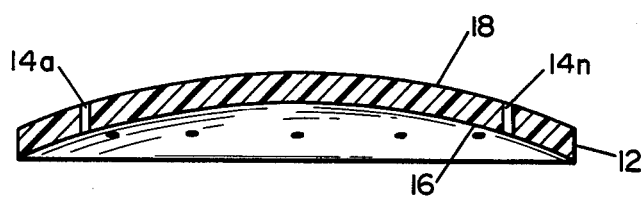
FIG. 2 illustrates a sectional view of FIG. 1.

FIG. 1 illustrates a corneal inlay 10 of polysulfone material or a like material where the material has a high refractive index with respect to that of the cornea which provides that a relatively thin corneal inlay can achieve a correction of several diopters. The polysulfone material is relatively permeable to the body nutrients and fluids. The polysulfone material also provides that the corneal inlay can be sterilized by an autoclave prior to insertion. The lens of the corneal inlay can have a thickness in the range of 0.1 mm to 0.4 mm, a diameter of approximately 3 mm to 7 mm, and includes a finite edge 12 as illustrated in FIG. 2. A preferred diameter would be 4.5 mm to 6.5 mm, while probably being slightly less than 6 mm in diameter. A plurality of holes or pores $14a$–$14n$ are provided about the edge of the corneal inlay, going through the corneal inlay, and having a diameter in the range of 0.001 mm to 0.1 mm. Any number of holes can be provided, and in this particular embodiment, by way of example and for purposes of illustration only, there are 12 holes equally spaced about the edge. This number of holes is illustrative. The surfaces of the inlay 10 are appropriately curved for a predetermined resolution. In the alternative, the holes can be randomly spaced so as not to be in a straight line.

FIG. 2 illustrates a sectional view, taken along section line 2 of FIG. 1 where all numerals correspond to those elements previously described. The figure also illustrates the bottom surface 16 and the top surface 18 of the corneal inlay, and the holes protruding between the two surfaces.

Figure 3:
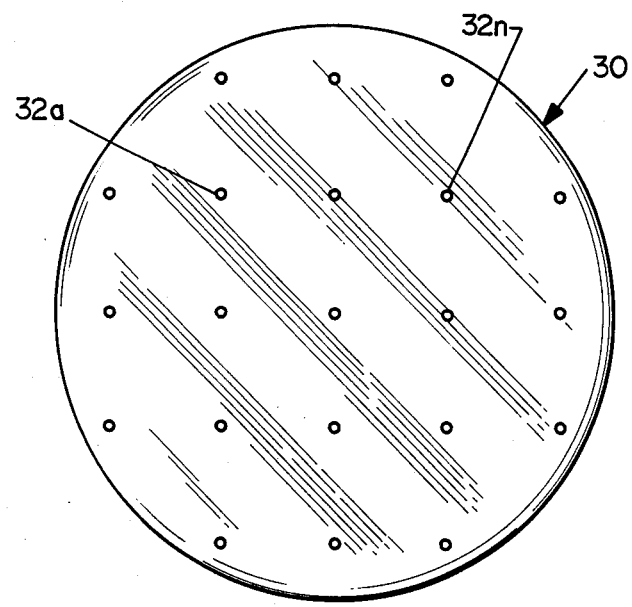
FIG. 3 illustrates a top view of a corneal inlay with a plurality of holes spaced about the surface area of the corneal inlay.

FIG. 3 illustrates a top view of the corneal inlay 30 with a plurality of holes $32a$–$32n$ randomly spaced about the surface of the corneal inlay and protruding through from the bottom layer to the top layer of the corneal inlay. The holes again are of a very small diameter with respect to the diameter of the corneal inlay so as not to be viewed by the individual during normal eyesight. The holes can also be clustered in groups, randomly spaced, or equally spaced dependent upon such parameters as hole diameter, hole spacing, and lens diameter.

Figure 4:
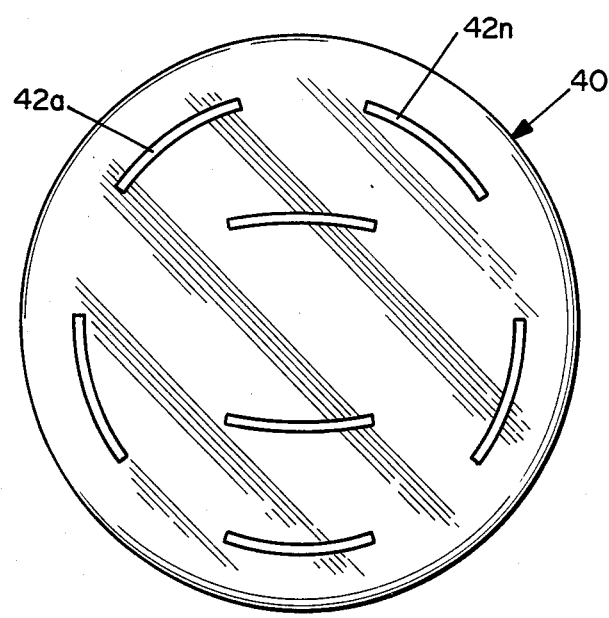
FIG. 4 illustrates a top view of a corneal inlay with a plurality of slits spaced about the surface area of the corneal inlay; and, FIG. 5 illustrates a non-porous corneal inlay of a specific size.

FIG. 4 illustrates a top view of a corneal inlay 40 with a plurality of longitudinal slits $42a$–$42n$ spaced about the surface area of the corneal inlay. The slits can have a width of 0.0001 mm to 0.1 mm and a length of 0.001 mm to 1.0 mm. While the slots are shown as being rectangular like in this configuration, this is by way of example and for purposes of illustration only and not to be construed as limiting of the present invention. The slots can assume any predetermined geometrical configuration and are not limited to the configuration as shown in the figure.

Figure 5:
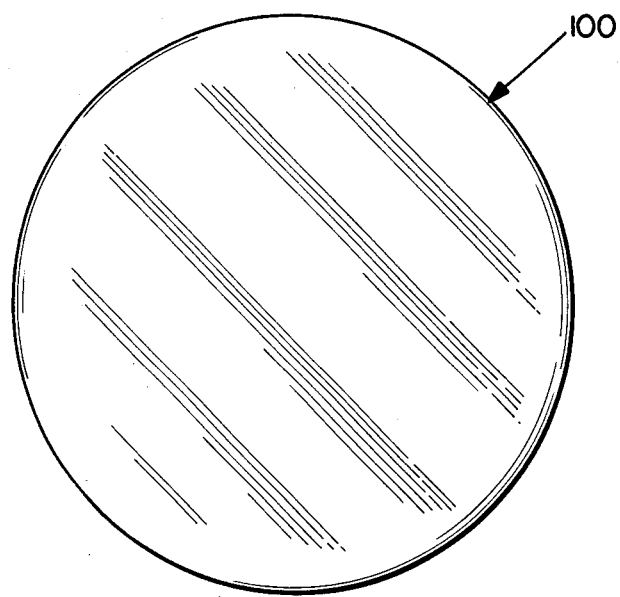

FIG. 5 illustrates a top view of a non-porous corneal inlay 100 of a suitable non-porous material. The physical shape is that as described for FIGS. 1–4 except that the corneal inlay 100 has no holes, and is of a non-porous type of material. The non-porous corneal inlay is of a diameter of 4 mm to 6.5 mm and of a thickness of 0.1 mm to 0.4 mm.

MODE OF OPERATION

The corneal inlay is implanted into the cornea by known surgical operative procedures. The corneal inlay can be sterilized before surgery or may come presterilized, such as by ETO. Surgical procedure basically comprises exposing the cornea by making a conjunctive flap around the periphery of the iris and then incizing the upper layer of the cornea for pealing back a small flap. A hollow pocket is formed between the layers of the cornea of sufficient size to receive the corneal inlay.

The holes or slits provide for nutrients, fluids, gases, etc. to pass from the bottom layer to the top layer of the cornea. Passage of the nutrients provides for continued viability of the corneal cells between the top surface of the cornea and the air.

I claim:

1. Corneal inlay comprising:
   a. an optic lens of a material for implant within the cornea; and,
   b. plurality of holes having a diameter from 0.001 mm to 0.1 mm extending from a bottom surface to a top surface for passage of nutrients through the cornea.
2. Corneal inlay of claim 1 wherein said holes are positioned about an edge.
3. Corneal inlay of claim 1 wherein said holes are positioned about the surface area.
4. Corneal inlay comprising:
   a. an optic lens of material for implant within the cornea; and,
   b. plurality of slits, having a maximum width of 0.01 mm to 0.05 mm and a maximum length of 0.05 mm to 1.0 mm, extending from a bottom surface to a top surface for passage of nutrients through the cornea.
5. Corneal inlay of claim 4 wherein said slits are positioned about an edge.
6. Corneal inlay of claim 4 wherein said slits are positioned about the surface.

* * * * *